United States Patent [19]

Casey

[11] Patent Number: 5,110,492

[45] Date of Patent: * May 5, 1992

[54] CLEANER AND DISINFECTANT WITH DYE

[76] Inventor: Irene Casey, P.O. Box 690566, Houston, Tex. 77269-0566

[ * ] Notice: The portion of the term of this patent subsequent to Jul. 7, 2007 has been disclaimed.

[21] Appl. No.: 566,549

[22] Filed: Aug. 13, 1990

Related U.S. Application Data

[60] Division of Ser. No. 227,178, Aug. 2, 1988, Pat. No. 4,965,063, which is a continuation-in-part of Ser. No. 936,171, Dec. 1, 1986, Pat. No. 4,793,988.

[51] Int. Cl.$^5$ .................. C11D 3/40; C11D 3/43; C11D 3/48; C11D 17/00

[52] U.S. Cl. ........................... 252/90; 252/99; 252/106; 252/156; 252/162; 252/408.1; 134/34; 134/40

[58] Field of Search ............. 252/99, 106, 107, 408.1, 252/162, 90, 156; 424/7.1, 44, 346, 45, 47, 347; 134/34, 40

[56] References Cited

FOREIGN PATENT DOCUMENTS 7231990 9/1972 France .

OTHER PUBLICATIONS

CAS abstract and listing with the equivalents of NL-7211429.

Primary Examiner—A. Lionel Clingman
Assistant Examiner—Erin M. Higgins
Attorney, Agent, or Firm—Vaden, Eickenroht, Thompson & Boulware

[57] ABSTRACT

A cleaning composition for surfaces which contains a disappearing dye which can include a germicide. The composition is packaged airtight. The dye is pH sensitive so that upon exposure to air the dye disappears. The delivery of the cleaner gives a visual check as to the surface contacted.

5 Claims, No Drawings

CLEANER AND DISINFECTANT WITH DYET

This application is a divisional of copening application Ser. No. 07/227,178, filed Aug. 2, 1988 now U.S. Pat. No. 4,965,063.

Which is application is a continuation-in-part of U.S. Ser. No. 936,171 filed Dec. 1, 1986 U.S. Pat. No. 4,793,988 for GERMICIDE AND DYE COMPOSITION and is related to several applications. The first related application was U.S. Ser. No. 738,082, filed May 24, 1985 for GERMICIDE AND DYE COMPOSITION AND METHOD, now abandoned. From Ser. No. 738,082, two continuation-in-part applications were filed, U.S. Ser. No. 936,171 and related case U.S. Ser. No. 935,236, filed Nov. 11, 1986, issued as U.S. Pat. No. 4,678,658 on Jul. 7, 1987.

BACKGROUND OF THE INVENTION

Cleaning compositions with and without a germicide are used on household and public surfaces such as counters, bathroom fixtures, tile surfaces and the like. The cleaning compositions typically include detergents, solvents and other additives such as fragrances. The cleaning compositions are liquids which may be diluted as needed. Other packaging includes aerosol mist, spray, wipes and foams.

Some cleaners include a germicide so that the surface is disinfected. Common disinfecting compounds used in cleaners are the quaternary ammonium compounds, phenols and alcohols.

The liquid cleaning compositions are generally clear or translucent. The mist sprays are clear and the foams are white in appearance.

SUMMARY OF THE INVENTION

The composition of this invention provides a cleaning product with a disappearing dye which can be sprayed in mist or foam delivery or otherwise spread on a surface with a wipe with the dye indicating the delivery of the cleaning product. Although the dye is added for color, it is thoroughly mixed and completely dispersed in the product so that a coating or fine layer imparts the visually colored product and will also indicate the surface contacted by the cleaning product. The cleaner can also contain one or more germicides. In the case of a cleaner and germicide combination, a visual check as to the surface receiving contact with the actual germicide will also be afforded.

The composition is a fluid. The cleaning composition can be a light duty type of cleaner utilizing only a surfactant or detergent system or can be a heavy duty cleaner including solvents. The composition is adjusted to an alkali pH value so that when packaged airtight the color is present. When the product is delivered to the surface, the colored composition loses color upon exposure to the atmosphere.

Germicides compatible with the pH environment of the product can be used such as the phenolic and quaternary ammonium compounds. Alcohols, which also act as solvents, can be used.

The composition can be packaged in any type of airtight container and delivery can be liquid, mist, aerosol spray or aerosol foam.

The composition can be used and applied as other cleaners/germicides. The dispenser can be for single or multiple applications depending on the usage desired.

DETAILED DESCRIPTION OF THE INVENTION

The product is manufactured as a liquid which can be packaged in a number of ways depending on the method of delivery, size of the container and surface location to be cleaned. Any type of airtight container for fluid delivery can be used. The typical delivery systems are spray, foam, pour and squirt for a cleaning aerosol and non-aerosol product. However, alternative systems such as a towelette or absorbent wipe containing the product in an airtight enveloping material such as sealed foil or other wrapping material could be used for a one time application. Any type of airtight packaging for use with a fluid cleaner can be used.

The basic cleaner product of this invention is a mixture of one or more surfactants (detergents) with the pH sensitive dye. The surfactant can be diluted with water to give the desired cleaning strength. The surfactant can be an anionic, nonionic, amphoteric or mixtures of the three types. Typical anionic surfactants used in cleaners are petroleum sulfonates, such as sodium dodecylbenzene sulfonate, alcohol sulfates such as sodium lauryl sulfate and ethoxylated higher fatty alcohol sulfates such as sodium lauryl ether sulfate. Typical nonionic surfactants are primary alcohol ethoxylates, secondary alcohol ethoxylates, alkyl phenol ethoxylates and alkanolamides. The amphoteric surfactants include a number of types of carboxylates derived from fatty imidazolines such as sodium dicarboxyethylcoco phosphoethyl imidazoline or fatty proprionates such as cocoamphoproprionate or cocoamphodipropionate.

The composition contains a dye which is dispersed into the composition. An example is the blue dye thymolphthalein which is a pH indicator colored at alkaline pH and upon neutralization becomes colorless. Any other dye color can be used that has the characteristics of the color change described herein. Other indicators which have the similar pH sensitivity can be used as shown, for instance, in the Table of "Indicators for Volumetric Work and pH Determination" in the Merck Index, 10th Ed. (1983).

The composition has the pH adjusted with the addition of an alkali system which can, in part, be the surfactant chosen and alkalis such as sodium hydroxide and/or potassium hydroxide. The color of the composition is noticeable when applied, but loses color after application. The pH sensitive dye was chosen for use by the consumer because the delivery of the alkaline composition in the environment causes the color to change in a relatively short period of time. The time of color change depends in part on the alkalinity of the product.

The color change is due to the neutralization of the composition from the acidic $CO_2$ in the air and the surface on which it is sprayed. The alkalinity of the composition is adjusted carefully so that neutralization of the composition can produce a visual change from blue, when using thymolphthalein, to clear within a short period of time. The pH value of cleaners ranges over the entire pH scale. Toilet bowl cleaners are mostly acidic with a pH value of 1.0 or less. Dish cleaners are more neutral with pH values of 6.0–8.0. Light duty all-purpose cleaners are usually slightly alkaline with pH values of 8.0–10.0. Heavy duty cleaners are often very alkaline with pH values of up to 14.0. Depending upon the pH value of the cleaner an appropriate dye indicator must be selected. The cleaning composition of this invention must be basic. The colored composition gives a visual check as to the area contacted with the cleaner making it easier to assure complete coverage and avoid skipping areas.

The composition of a basic cleaner of this invention would include the surfactant or mixture of surfactants at about 0.1% to about 20.0% percentage by weight basis. This is a typical range of surfactant for usage in a non-diluted product for household use. The amount of surfactant can be raised to a higher percentage if desired. Thymolphthalein in the range of about 0.01 to about 1% percentage by weight will give a broad range of blue color when varying intensity using an alkali system to adjust the pH of the composition from 9.3 to 14.0. The degree of alkalimity will affect the time period for neutralization and the color change. The typical range of dye is 0.05% to 0.07% by weight. The balance of the composition can be made up with water.

The basic cleaner composition can be foamed if packaged in the appropriate delivery system. A propellant must be added to the system. Any type of propellant can be used, however, the environmentally safe systems are generally hydrocarbons such as butane, propane, isobutane and mixtures thereof. A propellant system in the amount of about 5% to about 7% by weight will convert the liquid surfactant to a foam.

The basic cleaner composition can be augmented with a grease cutting solvent to produce a more heavy duty cleaning composition. The solvent is added to provide an effective ingredient for solubilizing residual water insoluble matter. For household use grease and oil solubilizers are used for cleaning surfaces. This invention intends to include all solvents used for household cleaning including glycol ethers, alcohols, chlorinated solvents such as methylene chloride, and petroleum derivative solvents. The solvent or mixed solvent system selected is added to the basic cleaner formula described above in he useful range of about 3% to about 20% percentage by weight. This range can be altered depending on the conditions of the soiled surface intended for use. A typical household cleaner has about a 7% solvent content. Some surfaces and finishes are sensitive to certain solvents. The selection of the amount and type of solvents used is directed by end usage.

The same type of dye system and pH adjustment is used for the cleaner with solvent. The composition can be foamed in the same manner with the same propellant additive. There are some components such as alcohol that require a higher amount of propellant for foaming so that a 5% to 25% by weight hydrocarbon propellant is required.

The composition of this invention can also include one or more germicides to produce a cleaner/germicide with disappearing dye. The delivery of the combination cleaner/germicide not only provides a visual check for cleaning but also for disinfection.

Household disinfectants that can be used are the quaternary ammoniums, phenols and alcohols. It is not intended to limit the type of germicide used in this invention as long as it is compatible with the other components of the cleaner. A cleaner may include the germicide and surfactant with or without a solvent.

The surfactant system must be compatible with certain germicides. The quaternary ammonium compounds must be used with a nonionic surfactant. The quaternary ammonium compounds are derived from benzalkonium chlorides; more specifically mixtures of alkyldimethylbenzylammonium chloride wherein the alkyl chain ranges from $C_8H_{17}$ to $C_{18}H_{37}$ and dialkylmethylbenzylammonium chlorides. Typically the alkyl chains predominating are $C_{12}H_{25}$, $C_{14}H_{29}$ and $C_{16}H_{31}$. Benzalkonium chlorides have a broad range of efficacy against both gram-positive organisms (such as *staphylococcus aureus*) and gram-negative organisms (such as *salmonella cholerasuis*). At lower concentrations they act as bacteriostats, in medium concentrations as sanitizers and in higher concentrations as disinfectants. They are widely used in hospitals in form of dilutions prepared from commercial concentrates. In the presence of hard water (400 ppm or more) the dialkyl quaternary ammonium compounds show greater efficacy in lower concentrations.

The quaternary ammonium compounds do not mix with the phenolic germicides discussed below. The quaternary ammonium compounds will foam and perform well at a high pH value. The quaternary ammonium compounds are used in a range of 0.05% to 5.0% by weight percentage. Benzalkonium chlorides have recognized germicidal activity in connection with a number of organisms. See *Encyclopedia of Chemical Technology*, (Third Ed.) John Wiley & Sons, Volume 7, Page 818, Table 9, "Bacteriostatic Dilutions of Benzalkonium Chloride".

The following are examples of formulations that can be prepared according to the description for a cleaner/germicide composition using quaternary ammonium compounds with disappearing dye. Each of Examples 1 and 2 can be foamed.

EXAMPLE 1

The ingredient listed in Table 1 are mixed and packaged in airtight aerosol containers with the propellant isobutane. A preferable glycol ether for use in these examples is ethylene glycol mono butyl ether. Some examples of the nonionic surfactants that can be used are: nonylphenol ethoxylate; polyethylene glycol laureth ether; and octylphenoxypolyethoxyethanol. Mixtures of various nonionic surfactants can be used. Prior to packaging the pH of the mixture is adjusted to about 12.5 with an alkali.

TABLE 1

| Components of Example 1 | |
|---|---|
| Ingredient | % Percent by Weight |
| Water | 85.85% |
| Glycol Ether | 7.00% |
| Nonionic surfactant | 2.00% |
| Benzalkonium chloride | 0.10% |
| Thymolphthalein | 0.05% |
| Isobutane | 5.00% |

EXAMPLE 2

The following Table 2 contains a list of ingredients which is mixed and pH adjusted in the same manner as Example 1 above.

TABLE 2

| Components of Example 2 | |
|---|---|
| Ingredient | % Percent by Weight |
| Water | 72.85% |
| Glycol Ether | 5.00% |
| Isopropanol | 8.00% |
| Benzalkonium chloride | 0.10% |
| Thymolphthalein | 0.05% |
| Nonionic surfactant | 2.00% |
| Sodium dicarboxyethylcoco phosphoethyl imidazoline | 5.00% |

TABLE 2-continued

| Components of Example 2 | |
|---|---|
| Ingredient | % Percent by Weight |
| Isobutane | 7.00% |

EXAMPLE 3

A composition of this invention can also be prepared using a component such as alcohol which serves as a solvent and a germicide. There is sufficient surfactant to foam the product if desired. The ingredients are mixed and pH adjusted as previously stated in Example 1. The A-70 is a hydrocarbon propellant.

TABLE 3

| Components of Example 3 | |
|---|---|
| Ingredient | % Percent by Weight |
| Isopropanol | 52.00% |
| Octylphenoxypolyethoxyethanol (Triton X-100) | 2.00% |
| Thylmolphthalein | 0.07% |
| Water | 25.93% |
| A-70 | 20.00% |

The general group of phenolic germicides can be used with a disappearing dye. The phenolic germicides must be used with anionic surfactants. The phenolic germicides include phenols with halogen substitution and additional aromatic groups and/or aliphatic groups added to the phenol nucleus. Phenolic compounds and their antimicrobial activity are well known. See *Encyclopedia of Chemical Technology* (Third Ed.) John Wiley & Sons, Volume 7, Pages 808-811.

The phenolic germicides can be included in a cleaner/germicide which foams if a detergent system of anionics is added. The phenols are added in the range of 0.05% to 5.0%. The following are examples of phenolic germicide/cleaners which are packaged as an aerosol spray. The propellant, isobutane, can be omitted if a nonaerosol product is desired.

EXAMPLE 4

The ingredients listed in Table 4 are to be mixed and packaged in an airtight aerosol container with the propellant isobutane. Prior to packaging the pH is adjusted to 12.5 with an alkali.

TABLE 4

| Components of Example 4 | |
|---|---|
| Ingredient | % Percent by Weight |
| Isopropanol | 8.00% |
| o-Phenylphenol | 0.10% |
| Glycol ether | 5.00% |
| Linear alkylaryl sulfonate | 0.80% |
| Thymolphthalein | 0.05% |
| Water | 81.05% |
| Isobutane | 5.00% |

EXAMPLE 5

The following ingredients are to be mixed, packaged and pH adjusted as stated in Example 4.

TABLE 5

| Components of Example 5 | |
|---|---|
| Ingredient | % Percent by Weight |
| Isopropanol | 8.00% |
| o-phenylphenol | 0.10% |

TABLE 5-continued

| Components of Example 5 | |
|---|---|
| Ingredient | % Percent by Weight |
| Glycol ether | 7.00% |
| Sodium dicarboxyethylcoco phosphoethyl imidazoline | 5.00% |
| Thymolphthalein | 0.05% |
| Water | 72.85% |
| Isobutane | 7.00% |

EXAMPLE 6

The following Example 6 is an additional formulation of a phenolic germicide/cleaner prepared according to Example 4.

TABLE 6

| Components of Example 6 | |
|---|---|
| Ingredient | % Percent by Weight |
| Glycol ether | 5.00% |
| o-phenylphenol | 0.10% |
| Sodium dicarboxyethylcoco phosphoethyl imidazoline | 5.00% |
| Thymolphthalein | 0.05% |
| Water | 84.85% |
| Isobutane | 5.00% |

Other ingredients may be added to the cleaner or cleaner/germicide products as desired. A fragrance may be added such as lavender, citrus or any mixture of essential oils or aromatics. Corrosion inhibitors may be added to composition packaged in metallic containers to maintain the integrity of containers. Inorganic detergent builders such as phosphates, silicates, carbonates and zeolites may be added to suspend loosened soil. In some cases a co-solvent system may be desired so that all the components are in one phase upon mixing so there is not stratification of the product.

The examples listed above are not intended to limit in any way the combination of ingredients of this invention. Other surfactants, solvents, germicides and additives can be substituted as long as the product has the disappearing color characteristics.

What is claimed is:

1. A composition for cleaning surfaces comprising: at least one surfactant;
    a pH sensitive dye which changes color upon exposure to air;
    an alkali means for adjusting the pH of the composition to an alkali pH to produce a color in the composition so that upon neutralization in the air the dye loses color;
    said composition being a visually colored composition with the disappearing pH sensitive dye effectively indicating the delivery of the composition and giving a visual check as to the area contacted when the visually colored composition is applied; and
    said composition packaged in a sealed air tight container adapted to maintain the alkali pH after the pH of the composition is adjusted to produce a color from the pH sensitive dye in the composition.

2. A composition of claim 1 wherein said surfactant is diluted with water.

3. A composition of claim 1 including an effective amount of a solvent for solubilizing residual water insoluble matter in the range of 0.1% to 20% by weight of the composition.

4. A composition of claim 1 including a fragrance.

5. A composition of claim 1 including an inorganic detergent builder.

* * * * *